United States Patent [19]
Lorenzen et al.

[11] Patent Number: 5,715,815
[45] Date of Patent: Feb. 10, 1998

[54] SHEATH STERILITY PRESERVATION FILTER AND SEAL FOR SUCTION CATHETERS

[75] Inventors: Rick D. Lorenzen, Ogden; Edward B. Madsen, Riverton, both of Utah

[73] Assignee: Ballard Medical Products, Inc., Draper, Utah

[21] Appl. No.: 599,665

[22] Filed: Feb. 12, 1996

Related U.S. Application Data

[63] Continuation of Ser. No. 412,472, Mar. 28, 1995, abandoned.

[51] Int. Cl.⁶ ............... A62B 7/10; A62B 18/08; A62B 23/02; A61M 5/00
[52] U.S. Cl. ............... 128/207.14; 128/205.12; 128/911; 128/912; 128/205.19; 128/207.16; 604/171; 604/281
[58] Field of Search ............... 128/200.26, 205.12, 128/207.14, 207.15, 207.16, 911, 912, DIG. 26, 205.19; 604/280, 163, 171, 281

[56] References Cited

U.S. PATENT DOCUMENTS

| | | | |
|---|---|---|---|
| 2,705,959 | 4/1955 | Elmore | 128/351 |
| 3,335,723 | 8/1967 | Waldman, Jr. | 128/214.4 |
| 3,444,860 | 5/1969 | Harrell | 128/349 |
| 3,757,771 | 9/1973 | Ruegg et al. | 128/2.1 E |
| 3,825,001 | 7/1974 | Bennet et al. | 128/214.4 |
| 3,894,540 | 7/1975 | Bonner, Jr. | 128/349 R |
| 3,902,500 | 9/1975 | Dryden | 128/351 |
| 3,937,220 | 2/1976 | Coyne | 128/276 |
| 3,991,762 | 11/1976 | Radford | 128/276 |
| 4,050,667 | 9/1977 | Kossett | 249/82 |
| 4,062,363 | 12/1977 | Bonner, Jr. | 128/349 R |
| 4,170,996 | 10/1979 | Wu | 128/349 R |
| 4,214,593 | 7/1980 | Imbruce et al. | 128/748 |
| 4,235,232 | 11/1980 | Spaven et al. | 128/214.4 |
| 4,326,520 | 4/1982 | Alley | 128/214.4 |
| 4,327,723 | 5/1982 | Frankhouser | 128/214.4 |
| 4,327,735 | 5/1982 | Hampson | 128/348 |
| 4,351,328 | 9/1982 | Bodai | 128/202.16 |
| 4,387,879 | 6/1983 | Tauschinski | 251/149.1 |
| 4,510,933 | 4/1985 | Wendt et al. | 128/207.14 |
| 4,569,344 | 2/1986 | Palmer | 128/207.16 |
| 4,634,433 | 1/1987 | Osbome | 604/171 |
| 4,638,539 | 1/1987 | Palmer | 29/157 R |
| 4,646,733 | 3/1987 | Stroh et al. | 128/207.16 |
| 4,669,463 | 6/1987 | McConnell | 128/207.14 |
| 4,696,296 | 9/1987 | Palmer | 128/207.16 |
| 4,805,611 | 2/1989 | Hodkins | 128/207.14 |
| 4,825,859 | 5/1989 | Lambert | 128/202.16 |
| 4,834,726 | 5/1989 | Lambert | 604/281 |
| 4,836,199 | 6/1989 | Palmer | 128/207.16 |
| 4,838,255 | 6/1989 | Lambert | 128/202.16 |
| 4,850,350 | 7/1989 | Jackson | 128/207.16 |
| 4,872,579 | 10/1989 | Palmer | 128/205.19 |
| 4,938,741 | 7/1990 | Lambert | 604/19 |
| 4,967,743 | 11/1990 | Lambert | 128/202.16 |
| 4,969,878 | 11/1990 | Schmidt et al. | 604/264 |
| 5,029,580 | 7/1991 | Radford et al. | 128/207.14 |
| 5,083,561 | 1/1992 | Russo | 128/207.16 |
| 5,088,486 | 2/1992 | Jinotti | 128/207.14 |
| 5,125,893 | 6/1992 | Dryden | 604/54 |
| 5,134,996 | 8/1992 | Bell | 128/207.14 |
| 5,140,983 | 8/1992 | Jinotti | 128/207.14 |
| 5,325,851 | 7/1994 | Reynolds et al. | 128/207.16 |
| 5,346,478 | 9/1994 | Jinotti | 604/171 |
| 5,490,503 | 2/1996 | Hollister | 128/205.12 |

*Primary Examiner*—Kimberly L. Asher
*Attorney, Agent, or Firm*—Workman Nydegger Seeley

[57] ABSTRACT

Filtration and closure barriers are disclosed which prevent passage of gas-carried contamination between the atmosphere and a collapsible sheath, which surrounds a catheter tube, during insertion and/or removal of the catheter tube from the respiratory tract of a medical patient.

3 Claims, 3 Drawing Sheets

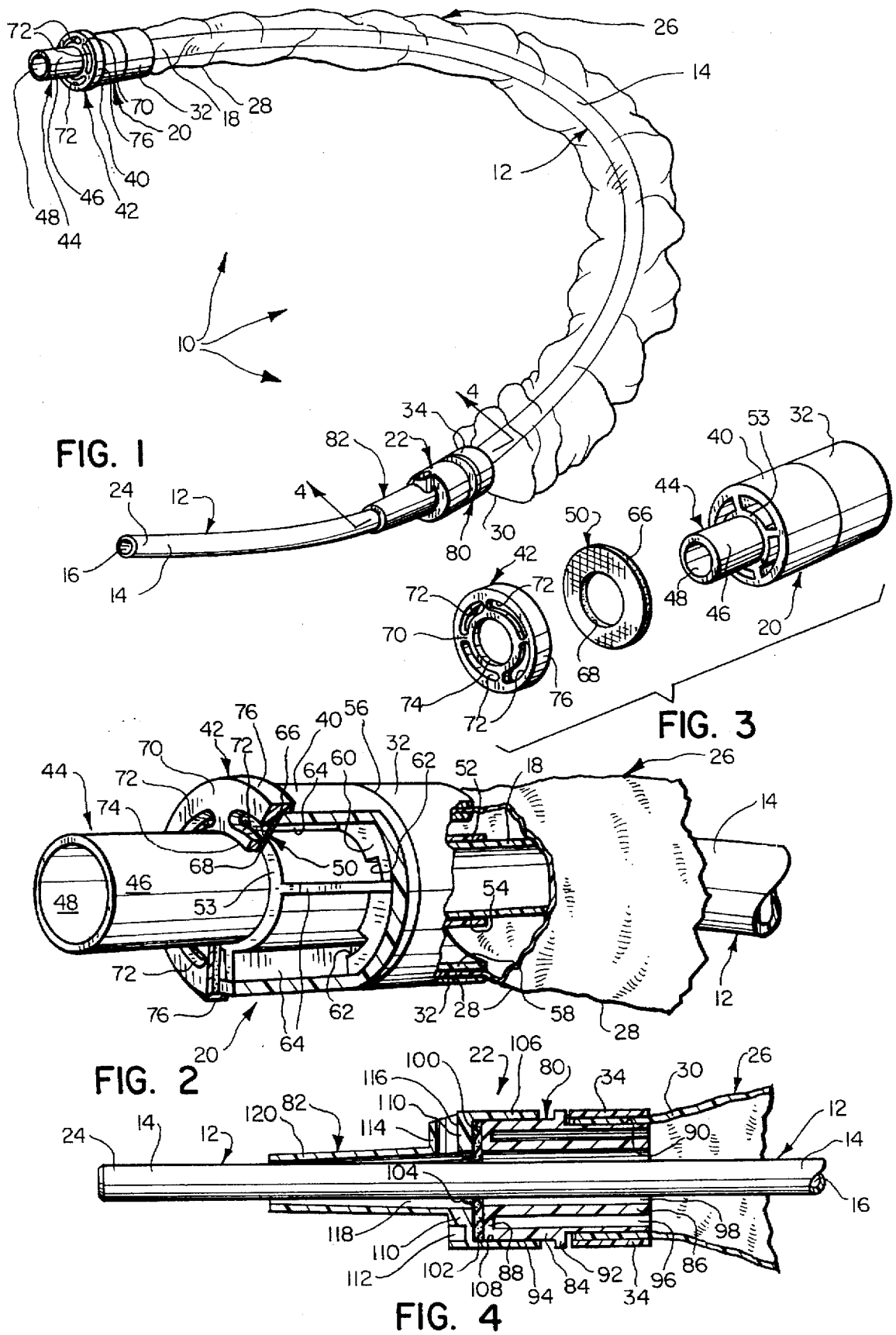

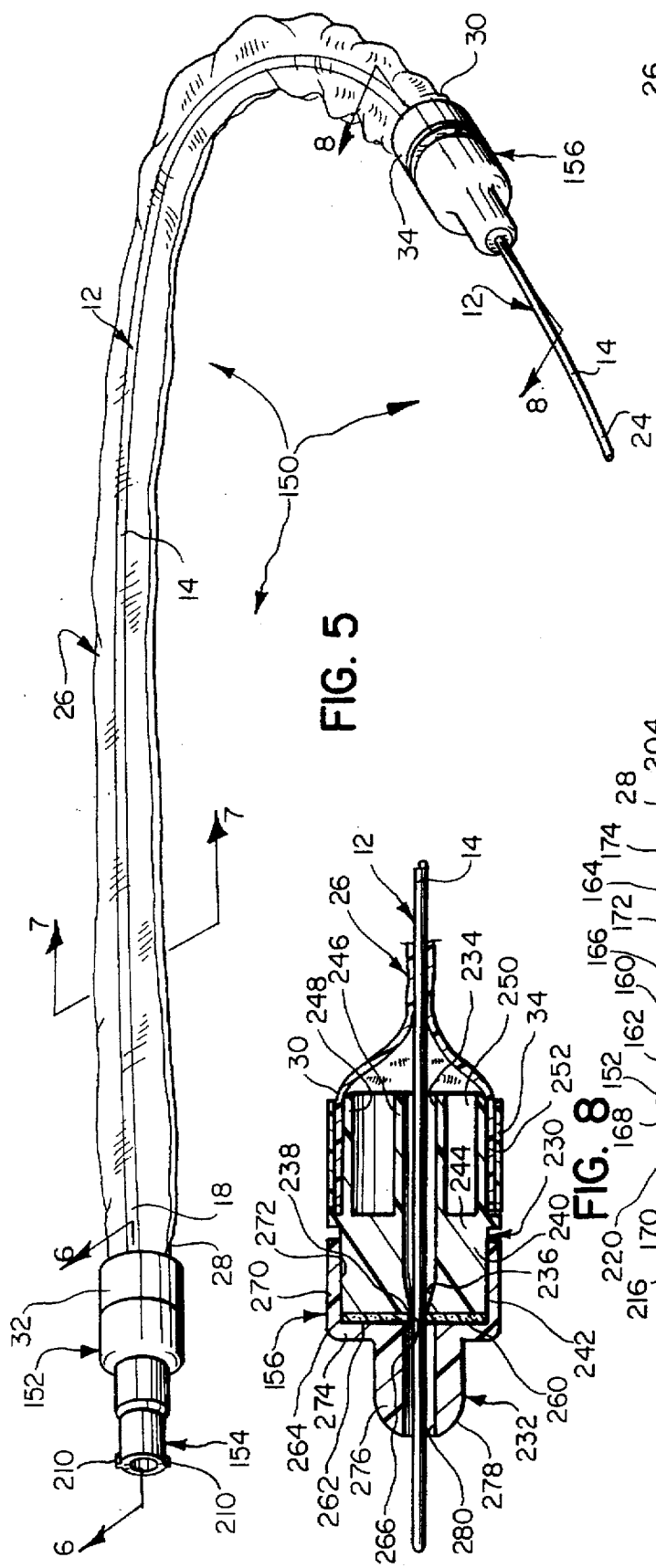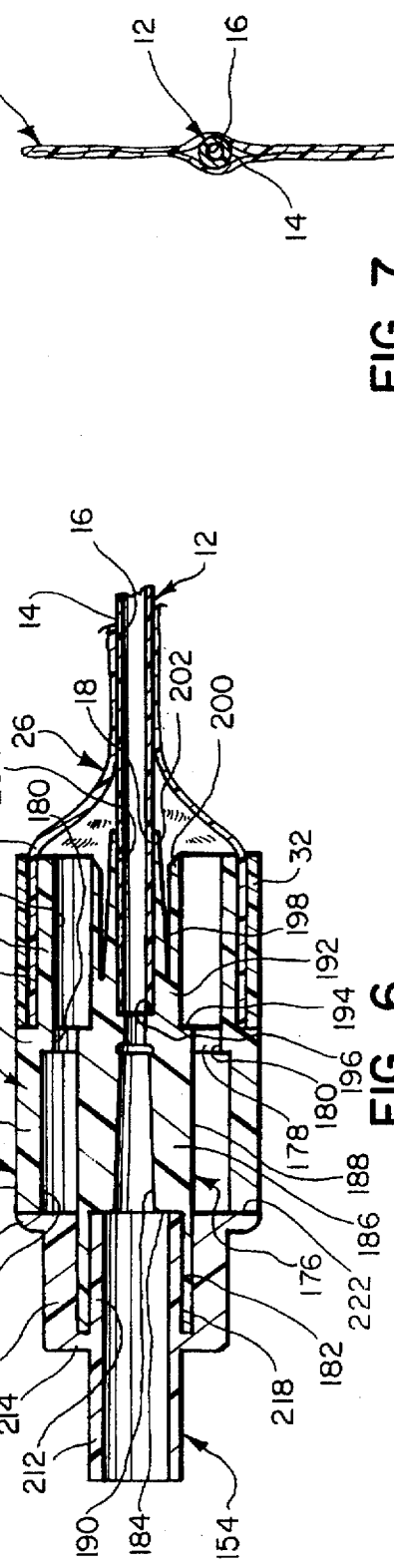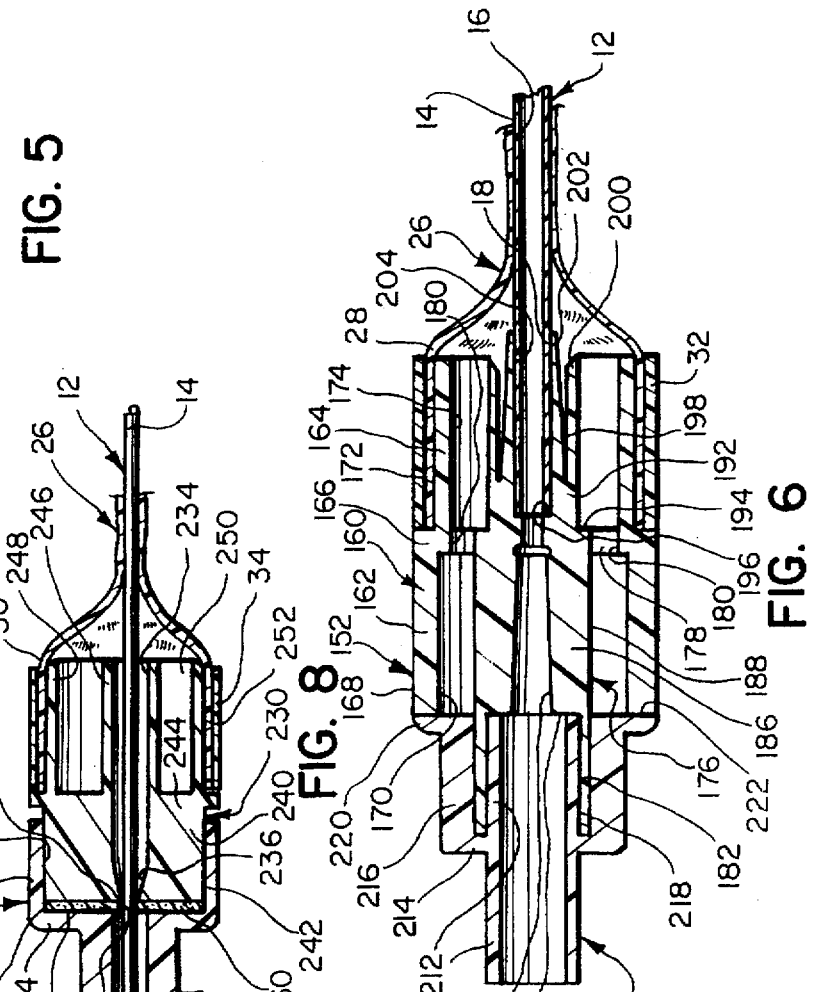

SHEATH STERILITY PRESERVATION FILTER AND SEAL FOR SUCTION CATHETERS

RELATED APPLICATIONS

This application is a continuation of application Ser. No. 08/412,472, filed Mar. 28, 1995, entitled "Sheath Sterility Preservation in a Respiratory Aspirating System and Related Methods," now abandoned.

FIELD OF INVENTION

The inventions disclosed herein relate generally to improved medical care for intubated patients, and more particularly to novel structure and methodology for preserving the sterility of an aspirating catheter tube-receiving collapsible sheath, bag or sleeve during one or more advancements into and retractions from the respiratory tract of an intubated patient.

BACKGROUND

Respiratory patient care is a dynamically developing field in medicine, ranging in its needs from infants to the aged. The range of respiratory ailments, both temporary and permanent, to which such patients are subjected, are many and varied. The frontier of medical knowledge is advancing and recommended treatments have become a blend of old and more recent discoveries.

Most problems now center or focus on multiple needs of the patient and accommodation of multiple treatments, some to be performed at the same time. The lack of equipment to facilely, efficiently, and safely accomplish the multiple therapies in the best interest of the patient has been and continues to be a concern. Other equipment problems also exist which concern preventing cost-oriented, unsafe extended use of ventilating, aspirating, and other respiratory access apparatus, reliability during use, quick and reliable removal and exchange of spent aspirating and ventilating devices without compromising the quality of health care provided to the patient, avoiding intentional or inadvertent conversion from a closed system to an open system, prevention of stress and/or occlusion of flow passageways to and from the patient's respiratory system, avoidance of a large inventory of a variety of incompatible products, providing easy, fail-safe access for multiple purposes.

By way of an example only, with low lung capacity patients, such as premature babies and adults suffering from emphysema, one problem is the removal of accumulated lung secretions without starving the patient for oxygen (thereby causing undesirable side effects) during the secretion removal process.

Sight must not be lost as to the deficiencies in prior proposals in terms of risks created for the health care provider. Largely, proposals of the past have ignored the needs of the health care provider to receive a reasonable measure of protection from contamination by the patient.

Providing apparatus and methodology having the capacity to promptly, efficiently, safely, and cost effectively address the health care needs of intubated patients across the entire spectrum of respiratory ailments comprises a largely unresolved need. The range of procedures comprise: ventilating, aspiration, oxygenation, sampling, visual inspection, in-line sensing, pressure monitoring, flushing, and medication and/or lavage. Better protection for the health care provider has been a long-term unsatisfied need as well.

In the past, a need has existed, notwithstanding sterilization at the time of manufacture, to evacuate and later receive gas from and into a collapsible sheath, bag, or sleeve during advancement therefrom into and retraction from within the patient's respiratory tract of the aspirating catheter tube initially stored within the sheath. This catheter tube advancement and retraction also displaces the sheath, which typically assumes a collapsed, accordion shape and thereafter an extended configuration.

When the aspirating catheter tube is withdrawn from the respiratory tract, following suctioning, the collapsed sheath is expanded which, in the past, has caused a limited amount of atmospheric gas to enter the sheath. This influent gas may be a source of potential if not actual contamination to the interior of the sheath and the exterior of the catheter tube.

Similarly, exhaustion of gas from within the sheath during catheter tube insertion has the potential to deliver contamination from the sheath to the health care provider.

Even though the ventilating and aspirating art is old, the last above-described problem has persisted for many years without an efficacious solution.

BRIEF SUMMARY AND OBJECTS OF THE INVENTION

In brief summary, the present invention overcomes or substantially alleviates problems of the prior art. For aspirating of the respiratory tract of a patient, with or without patient ventilation, an aspirating catheter tube is provided in a collapsible bag, sleeve, sheath or envelope. Initially, the catheter tube and the interior of the sheath are typically sterilized or subjected to a suitable anti-microbial treatment. To prevent later contamination due to atmospheric infiltration as the sheath is collapsed and expanded during insertion and removal of the catheter tube from the respiratory tract, the present invention, in its most elemental aspects, either filters influent atmospheric gas and effluent gas as it enters and leaves the sheath, or excludes gaseous influent or effluent flow into and from the sheath.

With the foregoing in mind, it is a primary object of the present invention to overcome or substantially alleviate problems of the prior art.

A further paramount object of the present invention is provision of structure and methodology which either filters influent and effluent gas introduced into and exhausted from a sheath which selectively surrounds an aspirating catheter tube or excludes influent and effluent flow of gas into and from the sheath.

These and other objects and features of the present invention will be apparent from the detailed description taken with reference to the accompanying drawings.

BRIEF DESCRIPTION OF THE DRAWINGS

FIG. 1 is a perspective of an aspirating catheter assembly, which embodies features of the present invention;

FIG. 2 is an enlarged fragmentary perspective, with parts broken away for clarity, of the proximal portion of the catheter assembly of FIG. 1;

FIG. 3 is an exploded perspective of said proximal portion of the catheter assembly of FIG. 1 with the catheter tube removed for clarity;

FIG. 4 is an enlarged fragmentary cross-section of the distal portion of the catheter assembly of FIG. 1 taken along lines 4—4 of FIG. 1;

FIG. 5 is a perspective of another aspirating catheter assembly, which also embodies features of the present invention;

3

Figure 9:
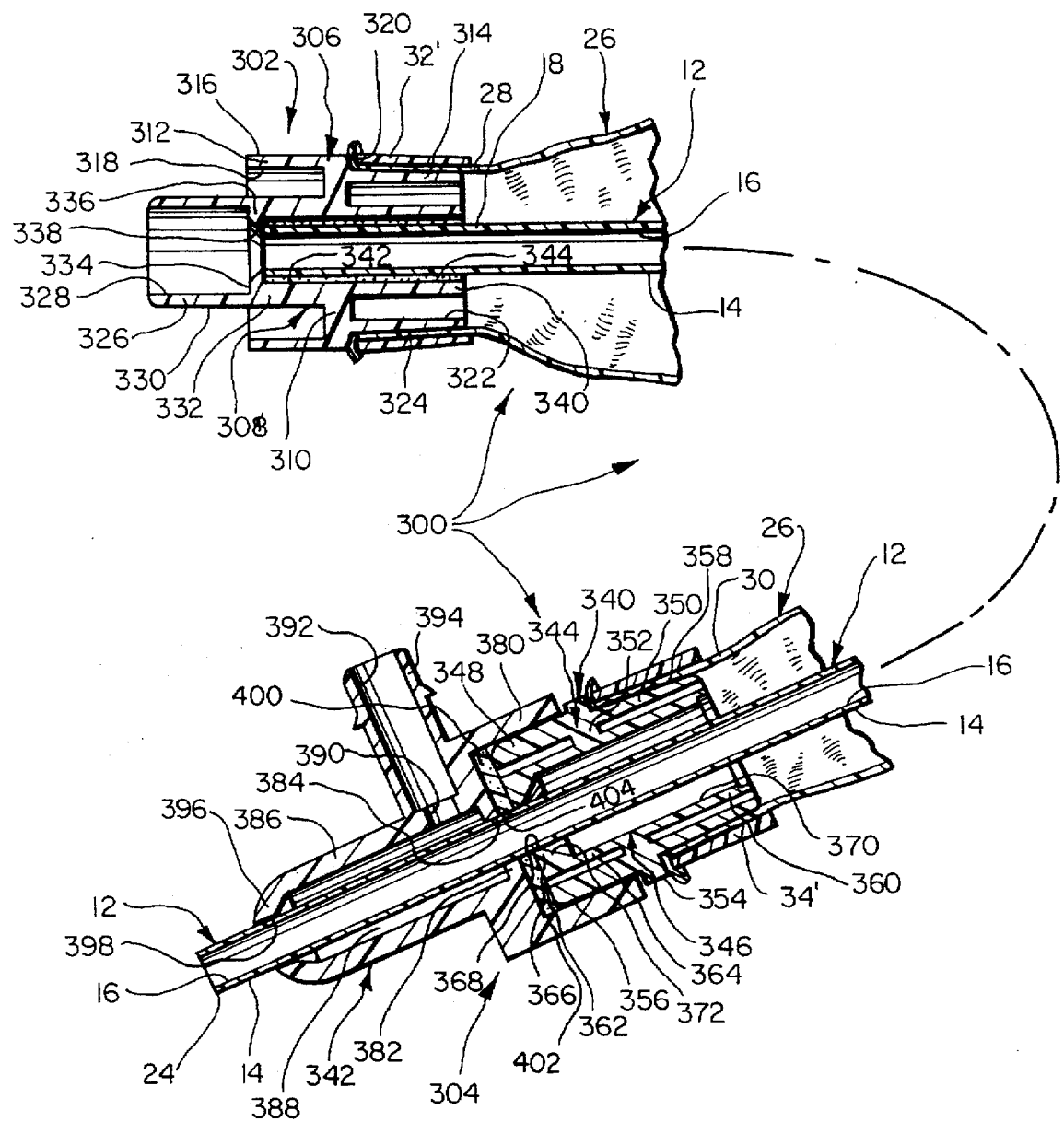

FIG. 6 is an enlarged fragmentary cross-section taken along lines 6—6 of FIG. 5;

FIG. 7 is an enlarged fragmentary cross-section taken along lines 707 of FIG. 7;

FIG. 8 is an enlarged fragmentary cross-section taken along lines 8—8 of FIG. 8; and FIG. 9 is an enlarged fragmentary cross-section of the proximal and distal portions of still another aspirating catheter assembly.

DETAILED DESCRIPTION OF THE ILLUSTRATED EMBODIMENTS

It is common practice in providing respiratory therapy to intubated patients that a catheter tube be inserted into the respiratory tract of a patient to aspirate secretions or deliver oxygen or medication, for example. Traditionally, the catheter tube is initially disposed co-extensively within a collapsible sheath, sometimes also called a bag, an envelope, or a sleeve. The sheath is collapsible for two purposes, i.e., (1) to allow the health care provider to grasp and manipulate the catheter tube through the sheath to accommodate insertion thereof into the respiratory tract of the patient, and (2) to allow end-to-end collapsing, in an accordion fashion, as a proximal fitting of the catheter assembly follows the catheter tube in a distal direction. It is standard practice to package and sterilize the catheter assembly after it is manufactured so that the interior of the sheath will be sterile prior to first use.

In the past, the advancement of the catheter tube accompanied by end-to-end collapsing of the sheath resulted in discharge of gas from within the hollow interior of the sheath. Similarly, the retraction of the catheter tube from the respiratory tract, after use, is accompanied by a proximal displacement of a proximal fitting of the catheter assembly so that the sheath is extended from its end-to-end collapsed condition to an extended condition, such as the one illustrated in FIG. 1. Such retraction of the catheter tube accompanied by the extension of the sheath, as explained above, has, using prior art proposals, been accompanied by influent flow of atmospheric gas into the hollow interior of the sheath with the attendant risk that such influent flow may introduce atmospheric contaminants, such as microbes.

Since catheter tube assemblies of the type in question are typically used several times before being removed, discarded, and replaced, the introduction of potentially contaminating atmospheric material into the sheath during catheter tube retraction and discharge of potentially contaminating gas from the sheath during catheter tube insertion has presented a long-term problem for which no satisfactory solution has been forthcoming prior to the present invention. The present invention provides barriers to the introduction into and discharge from the sheath of contaminants, including but not limited to microbes.

Reference is now made to the drawings wherein like numerals are used to designate like parts throughout. FIG. 1 illustrates an aspirating catheter assembly, generally designated 10. Catheter assembly 10 comprises a catheter tube, generally designated 12, illustrated as being of uniform wall thickness, and comprising an outside cylindrical surface 14 of uniform diameter throughout and an inside cylindrical surface 16, also of a uniform diameter throughout, which defines a hollow interior. The catheter tube 12 comprises a proximal end 18, which is non-displaceably anchored, by suitable bonding agent, adhesive, plastic welding technique or the like to the interior of a proximal catheter fitting, generally designated 20. The catheter tube 12 is slidable received by a distal fitting, generally designated 22, in sealed relation so as to accommodate extension of the distal end 24 of the catheter tube into the respiratory tract of a patient to a suitable location for accommodating removal of secretions, for example.

The catheter tube 12, or least a portion thereof, is at all times disposed within an enlarged, hollow sheath, generally designated 26, and formed of a suitable synthetic resinous film, which is collapsible for the purposes mentioned above. The synthetic resinous material from which the sheath 26 is formed is of medical grade and preferably transparent to accommodate easy viewing of the interior thereof by the health care provider of the interior of the sheath and the catheter tube 12 as well.

The sheath 26, as illustrated in FIG. 1, comprises a sleeve having a proximal end 28 and a distal end 30. The ends 28 and 30 are respectively superimposed contiguously over a reduced diameter portion of the fittings 20 and 22 followed by placement of a sleeve 32 and 34, respectively, over the respective end of the sheath 26 in compression-fit relation so as to prohibit gaseous flow between the hollow interior of the sheath and the atmosphere.

With continued reference to FIG. 1, proximal fitting 20 comprises a main boss or annular wall 40, which accepts a porous cap 42 at its proximal end. Cap 42 may be secured in the assembled position by gluing, bonding, welding, or the like. The fitting 20 also comprises a proximally extending tube generally designated 44, which accommodates connection of a source of suction for delivery of vacuum pressure to the catheter tube 12 at appropriate times under the control of a health care provider. The exposed portion of tube 44 is illustrated as being of uniform thickness comprising an exterior cylindrical surface 46 and an interior cylindrical surface 48 defining a hollow passageway.

The porous cap 42, when assembled, traps a washer-shaped filter 50 contiguously against both the proximal end of the boss 40 and the shoulder 53, as best illustrated in FIG. 2. The thickness of tube 44 is enlarged to strengthen the proximal fitting 20 at shoulder 53 and this greater thickness extends distally to a location just past radially-directed flange 60. Tube 44 extends completely through the fitting 20, but is further distally stepped to provide a diametrally smaller annular wall 52 into which the proximal end 18 of the catheter tube 12 extends and is preferably welded, bonded, or glued at interface 54. Thus, the proximal end 18 of the catheter tube 12 is fixedly joined to the proximal fitting or connector 20 against relative rotation and axial displacement.

The main boss or annular wall 40 is stepped at shoulder 56. Shoulder 56 merges as one piece with a diametrally reduced annular wall 58, which contiguously receives the proximal end of the sheath 26 over which the annular collar 32 is compression-fit so that flow of gas between the atmosphere and the interior of the sheath 26 adjacent the collar 32 does not occur.

A support spacer or flange 60 is formed as one piece with wall 40 and tube 44. Flange 60 extends in a radial direction, but is interrupted by a series of spaced slots 62 to accommodate selective passage of gas, as explained hereinafter.

In addition to the radial support afforded by annular wall or flange 60, a series of spacers 64, each extending axially between the wall 40 and tube 44, are provided. Spacers 64 are illustrated as being spaced 90° from each other, although other configurations could be used. Also, spacers 64 are disposed directly adjacent the slots 62, but slightly out of alignment therewith.

The washer-shaped filter 50 comprises a commercially available anti-microbial free mesh filter media of medical grade so that the filter will remove all atmospheric contaminants including microbes from influent gas from the atmosphere passing through the filter.

The washer-shaped filter 50 is illustrated as being sized so that the outer peripheral edge 66 has a diameter substantially the same as the outer diameter of the cylindrical wall 40 and the inner edge 68 has a diameter slightly less than the outside diameter of tube 44, at surface 46, so as to be received snugly over surface 46 to prevent short-circuiting airflow along the edge 68.

Cap 42 is generally annular or ring-shaped in its configuration, comprising an annular radially disposed base wall 70 in which arcuate lobe-shaped apertures 72 are disposed. Radially-directed wall 70 comprises an annular internal edge 74, defining a central aperture the diameter of which is either the same or slightly less than the outside diameter of tube 44 to insure a snug gas impervious fit between the two when assembled, as illustrated in FIG. 1 and 2.

While the proximal side of annular wall or flange 70 is exposed to the atmosphere, the distal side contiguously engages the proximal face of the filter 50, as best illustrated in FIG. 2, when the accessory assembly 10 is fully assembled.

Flange wall 70 merges as one piece with annular, axially-directed exposed flange 76. The unstressed internal diameter of flange 76 is slightly less than the diameter of edge 66 and the outside diameter of wall 40 so as to accommodate a press-fit relationship.

It is to be appreciated that the catheter assembly 10 of FIG. 1 is typically used in conjunction with other devices. For example, a conventional suction control valve may be mounted at tube 44 or tube 44 may be connected to a suction tube which in turn connects to a conventional suction control valve.

In addition, distal fitting 22 is adapted to be inserted into a fitting associated with the patient, such as an adapter connected to an exposed end of an indwelling tracheal tube. The fitting 22 may be glued in this assembled condition. When so connected, at appropriate times, the health care provider will grasp the catheter tube 12 through the sheath 26 and advance the catheter tube 12 into the respiratory tract of the patient, for example, to remove secretions from the lungs. As the catheter tube 12 is advanced, the sheath 26 collapses, somewhat in an accordion fashion, end-to-end, as fitting 20 is moved closer and closer to fitting 22. This typically causes gas disposed within the hollow interior of the sheath 26 (outside the catheter tube 12) to be expelled to the atmosphere through slots 62, along the spaces between axially-directed spacers 64 and through the filter barrier 50 at apertures 72. Filter barrier 50 prevents any contamination within the sheath from reaching the health care provider.

When the catheter tube 12 is withdrawn from the respiratory tract, fitting 20 is displaced progressively a greater and greater distance from fitting 22, which once more extends the sheath 26 from its end-to-end collapsed condition toward the position illustrated in FIG. 1. As this retraction occurs, atmospheric gas passes through apertures 72, filter barrier 50, along the spaces between axially-directed spacer 64, and through the slot 62 into the hollow interior of the sheath 26 (outside the catheter tube 12). Filter barrier 50 removes atmospheric contaminants, including microbials, so that the hollow interior of the sheath 26 and the exterior of the catheter tube 12 are not contaminated by influent atmospheric gas.

Reference is now made to FIG. 4 which illustrates, in enlarged cross-section, distal fitting 22. Distal fitting 22 comprises the previously mentioned compression-fit collar 34, a double wall sleeve, generally designated 80, and a distal wash housing, generally designated 82.

Double sleeve 80 comprises an outside, generally annular wall 84, and an inside annular wall 86. The two walls are joined one to another by a radially-directed distal annular flange 88, which is formed as one piece with annular walls 84 and 86. Walls 84 and 86 extend axially in concentric spaced relationship. The flange 88 forms a fulcrum which accommodates radial flexure of the wall 84, making it easier to place the proximal end 30 of the sheath 26 contiguously over annular surface 90 and to receive collar 34 in compression-fit, impervious relation. To accommodate the flexure desired, the thickness of the portion of the wall 84 within the collar 34 is diametrally reduced. A radially-directed ring 92 strengthens the annular wall 84 and forms a location of demarcation between the distal thicker portion of wall 84 and the proximal thinner portion of wall 84. The diameter of annular surface 94 is larger than the diameter of surface 90 of wall 84.

An annular space 96, in the form of a bind groove, exists between walls 84 and 86. Wall 86 defines a hollow interior 88 between the wall 86 and the exterior surface 14 of the catheter tube 12 to accommodate ease of displacement of the catheter tube 12 in the manner described above.

An elastomeric washer 100 is contiguously disposed at the distal surface of wall 88. Washer 100 is held compressively and comprises an annular outside edge 102, the diameter of which is substantially the same as the diameter of surface 94. Washer 100 comprises an interior centrally disposed aperture at edge surface 104, the diameter of which is substantially less than the diameter of the outside surface 14 of the catheter tube 12. Accordingly, the washer seal 100 compression-fits at surface 104 against the outside surface 14 of the catheter tube 12, as illustrated in FIG. 4, so as to prevent flow of gas along the outside of the catheter tube 12 between the atmosphere and the interior of the sheath 26. In addition, the washer 100 functions as a wipe, due to its compression-fit relationship with the outside surface 14 of the catheter tube 12. Thus, when catheter tube 12 is withdrawn from the respiratory tract of a patient, any residual debris, including secretions, carried at the outside surface 14 is removed by the wiper/seal 100 and left on the distal side of the washer/seal 100.

Wash housing 82 comprises a cup-shaped proximal end including an annular axially-directed exposed flange 106, the inside surface of which comprises substantially the same diameter as surface 94 and which is secured in place by welding, glue, bonding or the like at interface 108. The location of flange 106 in respect to wall 84 is such as to provide an appropriate space for washer 100, as illustrated in FIG. 4.

Preferably, housing 82 is transparent to allow visual inspection of secretions and other debris wiped by washer 100 from the exterior surface 14 of catheter tube 12 during retraction or withdrawal of catheter tube 12 from the respiratory tract of the patient. Wash housing 82 further comprises a generally annular radially-directed flat wall 110 which merges as one piece with axially-directed proximally-extending flange 106. To reduce material used, a curvilinear groove 112 is placed in wall 110. Wall 110 merges with a radially-directed annular wall 114, the interior of which is hollow at passageway 116. Annular wall 114 terminates internally at a port spaced from the exterior surface 14 of catheter tube 12. The interior of the wash housing 82 comprises a hollow debris-receiving chamber 118. The passageway 116 is adapted to accommodate entry of wash water with which the removed debris in chamber 118 is mixed with the irrigation solution and thereafter the mixture is suctioned away through the distal end 24 of the catheter tube 12. If desired, various known irrigation appliances may be connected at port 116 to accommodate introduction of irrigation liquid.

Walls 110 and 114 are formed as one piece with a distally-directed hollow spout or catheter tube guide 120, illustrated as being divergently tapered in a distal direction. Tapered wall 120 is illustrated as being of uniform thickness and is sized, shaped, and configurated so as to accommodate insertion into a manifold, connector, adapter, or the like carried, for example, by an exposed end of an indwelling tracheal tube. The fitting 22 may be glued, welded, bonded or the like, for example, to a manifold or other fitting carried at an exposed end of an indwelling tracheal tube to accommodate insertion and retraction of the catheter tube 12 when and as deemed appropriate by the health care provider.

Reference is now made to FIGS. 5 through 8 which illustrate a second catheter assembly, generally designated 150, which embodies principles in accordance with the present invention. Specifically, catheter assembly 150 may be used for neonates and to deliver liquid medication and comprises the previously described catheter tube 12, shown to be diametrally smaller, comprising exterior surface 14 and hollow sheath 26, assembled in a flat condition with a minimal gas content therein. Catheter assembly 150 further comprises a proximal fitting generally designated 152, which receives previously described compression-fit collar 32 to hold proximal end 28 of the sheath 26 to the proximal fitting 152 in impervious relation. Fitting 152 comprises a luer adapter, generally designated 154, by which medication is selectively introduced by the health care provider through the catheter tube 12 into the respiratory tract of a medical patient, for example, by infusion from a syringe. The luer adapter 154 comprises opposed male luer fittings 210 formed as one piece with annular wall segment 212.

Catheter assembly 150 further comprises a distal fitting 156 over which the distal end 30 of the sheath 26 is superimposed and receives previously described sheath retaining collar 34 in compression-fit relation.

Proximal fitting 152 is best illustrated in FIG. 6 and comprises a stepped outer wall 160 comprising a somewhat diametrally larger proximal segment and a somewhat diametrally smaller distal segment, 162 and 164 respectively. Segment 162 joins segment 164 centrally at annular dog-leg or stepped segment 166. Wall segment 162 is annular and is illustrated as being of uniform thickness throughout comprising an outside diameter at annular surface 168 and an inside diameter at internal annular surface 170. Wall segment 164 defines an outside diameter at surface 172 and an inside diameter at surface 174.

The proximal end 28 of sheath 26 is superimposed over surface 172 contiguously followed by compression-fit placement of collar 32 into the position illustrated in FIG. 6 such that collar 32 compressively joins the proximal end 28 of sheath 26 along a substantial length thereof in a substantially flat manner, which hermetically seals the proximal end 28 of the sheath 26 against gaseous flow between wall segment 164 and collar 32.

Proximal fitting or connector 152 is formed preferably using injection molded techniques as one piece from a suitable synthetic resinous material and further comprises an internal wall, generally designated 176. Wall 176 is connected as one piece to wall 160 by a central internal radially-directed flange or wall 178, illustrated as being apertured at spaced locations 180. If desired, the apertures 180 can be eliminated, since fitting 152 prohibits any gaseous flow into or out of the interior of the sheath 26.

Interior generally annular wall 176 is stepped and bifurcated. More specifically, wall 176 comprises a proximal ring or boss 182 illustrated as comprising an annular wall having a uniform thickness. Ring or wall 182 merges at shoulder 184 with a thicker wall segment 186, the exterior surface 188 of which has a uniform diameter and the interior surface 190 defines a hollow passageway for liquid medication, which passageway is conically convergent in a distal direction.

Wall segment 186 merges with distal wall segment 192 at shoulders 194 and 196, respectively. Reduced thickness wall segment 192 is bifurcated at 198 into distally-directed annular extensions 200 and 202. The interior diameter of extension 202 at surface 204 is substantially the same as the diameter of catheter tube surface 14. The proximal end 18 of the catheter tube 12 is snugly fit into the hollow interior defined by surface 204 and is there secured by gluing, bonding, or welding against either rotational or axially relative displacement.

Thus, when assembled, the hollow interior at 16 of the catheter tube 12 is in fluid communication with the hollow interior of chamber 190. Wall segment 212 extends the full length of the adapter 154, being externally interrupted by outwardly-directed radial wall 214. Radially-directed wall 214 is essentially centrally disposed along wall 212 and merges as one piece with annular axially-directed wall 216. Wall 216 is illustrated as having a uniform outside and inside diameter defining an annular blind groove 218 into which wall segment 182 is inserted and retained against relative displacement, for example, by gluing, bonding, welding or the like. Thus, luer adapter 154 is integrally joined to proximal fitting 152 against relative displacement.

Wall 216 merges into outwardly-directed radial flange 220, the maximum outside diameter of which substantially equals the diameter of surface 168. Flange 220 is integrally joined at interface 222 to the proximal edge of wall segment 162 so as to prohibit any gaseous flow through the fitting 152 between the atmosphere and the interior of the sheath 26 for example, by gluing, welding, bonding or the like. Thus, with the exception of flow through chamber 190 and catheter tube 12, the fitting 152 in conjunction with luer adapter 154 comprise an impervious closure which prevents flow of gas between the atmosphere and the interior of the sheath 26.

Distal fitting 156 is illustrated best in FIG. 8 and comprises previously mentioned collar 34, central component generally designated 230 and distal tip generally designated 232. Central fitting 232 comprises a body of material defining a hollow chamber 234, the distal end of which is tapered at 236 to define a small distal opening at 238. Fitting 230 comprises a distal segment 240, the exterior cylindrical surface 242 of which has a pre-determined diameter. Distal wall segment 240 merges at location 244 into spaced proximally-directed annular walls 246 and 248. Walls 246 and 248 are concentric, of uniform thickness, and define a blind groove 250 therebetween.

The exterior cylindrical surface 252 of wall 248 comprises a diameter substantially the same as the diameter of surface 242, over which the distal end 30 of the sheath 26 is contiguously placed prior to reception of the compression-fit collar 34, which compressively joins the distal end 30 of sheath 26 along a substantial length thereof in a substantially flat manner so as to create an impervious relation between wall segment 248 and collar 34 thereby prohibiting flow of gas between the atmosphere and the interior of the sheath 26.

Distal segment 240 of fitting 230, at the distal surface 260 thereof contiguously receives a washer-shaped elastomeric wiping seal 262. Seal 262 comprises an outer annular edge 264 the diameter of which is substantially the same as the diameter of surface 242. Washer 262 defines a central aperture 266 through which the catheter tube 12 passes. Aperture 266 has a diameter slightly less than the diameter of the exterior surface 14 of the catheter tube 12 so that a compression relationship is created between the washer 262 and the exterior surface 14 of the catheter tube 12. This tight fit prevents flow of gas across surface 266 between the atmosphere and the interior of the sheath 26. Washer 262 wipes any debris carried at the exterior surface 14 of the catheter tube 12 when and as the catheter tube is withdrawn from the respiratory system of the patient.

The seal/wiper 262 is held in the position illustrated in FIG. 8 between the tip 232 and connector 230. Tip 232 comprises a proximally-directed cup-shaped portion comprising an axially-directed proximally-extending exterior flange 270 the interior diameter of which is substantially the same as the diameter of surface 242. Flange 270 is secured against rotational and axially displacement in respect to fitting 230 by gluing, bonding, welding or the like at interface 272.

Flange 270 merges with a radially-directed wall 274, which in turn merges with a hollow wall 276. Wall 276 comprises an exterior diameter substantially less than the mean diameter of the flange 270 and is tapered at distal tip surface 278. Wall 276 and tip 278 comprise a hollow interior at 280, the diameter of which is substantially greater than the diameter of surface 14 of catheter tube 12. Wall 276 and tip 278 are sized, shaped, and located so as to accommodate insertion into a fitting, adapter, or manifold carried at an exposed end of an indwelling tracheal tube, for example. The male portion 232 may be secured in the inserted position by gluing, bonding, welding, or the like.

As mentioned above, during assembly, gas which otherwise might be disposed within the interior of sheath 26 is evacuated, for example, by manually flattening the sheath either before any fitting is attached to either end of the sheath or after one such fitting has been attached. By so evacuating gas which otherwise would be initially disposed within the sheath 26, insertion of the catheter tube 12 into the respiratory tract of the patient is not accompanied by discharge of gas from the interior of the sheath 26, although the sheath collapses end-to-end as the proximal fitting 152 is moved closer and closer to the distal fitting 156. Fitting 152 in conjunction with adapter 154 prevent flow of gas from the interior of the sheath 26, as does fitting 156, during catheter tube insertion.

When the catheter tube 12 is withdrawn from the respiratory tract, similarly, no gas from the atmosphere flows into the hollow interior of the sheath 26, although the sheath 26 is extended from its collapsed accordion shape toward and into the extended position of FIG. 5 as proximal fitting 152 is moved farther and farther away from distal fitting 156. Thus, by using barriers in the form of impervious fittings or connectors, contamination is prevented from entering or leaving the interior of sheath 26.

Reference is now made to FIG. 9 which illustrates a further aspirating catheter assembly, generally designated 300, embodying principles of the present invention. Catheter assembly 300 comprises catheter tube 12, the sheath 26, a proximal fitting, generally designated 302, which comprises collar 32' and a distal fitting, generally designated 304, which comprises a tapered collar 34'.

With specific reference to the top portion of FIG. 9, fitting 302 is illustrated in cross-section and comprises a completely impervious barrier to flow of gas between the atmosphere and the interior of the sheath 26. Fitting 302 comprises an exterior generally cylindrical or annular wall segment generally designated 306 and an interior generally annular wall segment, generally designated 308. Wall segments 306 and 308 are formed as one piece with radially-directed wall 310, which extends between wall segments 306 and 308. Wall segment 306 comprises a proximal wall portion 312 and a distal wall portion 314. Wall portion 312 is illustrated as being of uniform thickness and comprises an exterior cylindrical surface 316 and an interior cylindrical surface 318. Wall portion 312 merges with wall portion 314 at radial wall 310 where there exists a shoulder 320. Wall segment 314 comprises an annular surface 322 forming the inside surface thereof and an outside surface 324, which is divergently tapered in a distal direction.

Internal wall 308 comprises a proximally-directed extension 326 which comprises a hollow interior 328 and an exterior surface 330 by which an aspirating suction tube or a suction control valve is connected to selectively deliver vacuum pressure to the hollow interior at 16 of the catheter tube 12. Extension 326 merges into wall segment 332 at shoulder 334. Shoulder 334 comprises part of an inwardly-directed radially oriented wall 336 in which a counterbore 338 is disposed. Wall segment 332 merges as one piece with distally-directed wall segment 340. The internal surface 342 is cylindrical and continuous across both wall portions 332 and 340. The proximal end 18 of the catheter tube 12 is illustrated as being inserted concentrically within the hollow region formed by wall surface 342 and is secured against relative movement, either in an axially or rotational direction by bonding agent, glue, or the like placed at interface 344. The spaced relationship or gap between wall portions 306 and 308 accommodate reduction in the amount of material consumed in forming proximal fitting or connector 302. Also, the cantilevered nature of relatively thin wall portion 314 accommodates yieldability or deflection which assists in super-positioning the proximal end 28 of the sheath 26 over the exterior surface 324 and in placing the slightly tapered collar 32' into compression-fit relation over end 28 as best illustrated at the top of FIG. 9. In this manner, collar 32' compressively joins the proximal end 28 of sheath 26 along a substantial length thereof in a substantially flat manner to form a hermetic seal that prevents gases from entering into or exiting from the enclosed area between catheter 12 and sheath 26 at the proximal fitting 302. Thus, fitting 302 creates a barrier against gaseous flow therethrough.

Specific reference is now made to the lower portion of FIG. 9, which illustrates in cross-section the details of distal fitting 304. Distal fitting 304 comprises a collar 34', a fitting, generally designated 340, and a male connector member, generally designated 342. Fitting 340 comprises two concentric generally annular wall portions, generally designated 344 and 346, respectively. Wall portion 344 is external to wall portion 346 and comprises a thicker distal segment 348 and a proximal reduced thickness wall segment 350. Both wall segments 348 and 350 are annular in their disposition and are connected together as one piece at a central radially-directed wall segment 352. Wall segment 352 terminates in an exposed annular rib 354. Wall segment 348 at exterior annular surface 356 defines the largest diameter portion, exclusive of rib 354, of connector 340. Cantilevered wall segment 350 is annular and rearwardly convergent, comprising a tapered exterior wall surface 358. The dimensional nature of wall segment 350 allows for yieldability or deflection to accommodate compression-fit placement of the collar 34' after the distal end 30 of the sheath 26 has been contiguously placed upon surface 358. In this manner, collar 34' compressively joins the distal end 30 of sheath 26 along a substantial length thereof in a substantially flat manner to form a hermetic seal that prevents gases from entering into or exiting from the enclosed area between catheter 12 and sheath 26 at the distal fitting 304. Similarly, cantilevered wall segment 348 accommodates a limited amount of flexure for purposes of connection to male member 342.

Wall segment 346 comprises a cantilevered annular wall segment 360, illustrated as having a uniform thickness throughout, with the exception of a stepped configuration at the proximal edge thereof. Wall segment 346 also comprises a cup-shaped distal segment 362 comprised of annular wall segment 364 and distal radially-directed wall 366. Wall 366 is apertured at site 368, the diameter of which is preferably slightly less than the outside diameter of catheter tube 12 at surface 14. The interior surface 370 is co-extensive along wall segments 360 and 366. Wall surface 370 comprises or defines a hollow interior of connector 340 the diameter of which is substantially greater than the outside diameter of catheter tube 12 at surface 14. The hollow interior defined by surface 370 merges with a conically-shaped or counterbore 372, which forms the proximal surface of wall 366.

In addition to accommodating placement of the tapered sheath-retaining collar 34' in compression-fit, impervious relation, connector 340 accommodates assembly of the male member 342 to the connector 340.

Male member 340 comprises a proximally-directed annular flange 380, the interior diameter of which is substantially the same as the diameter of surface 356, accommodating insertion of wall segment 348 and adherence therein in non-displaceable relation by use of adhesive, bonding agent, plastic welding, or in any other suitable fashion.

Annular flange 380 merges with a radially-directed wall 382. Wall 382 is interrupted by a centrally disposed aperture 384, the size of which is preferably slightly less than the diameter of the catheter tube 12 at exterior surface 14. Accordingly, both aperture 384 and aperture 364 snugly engage the exterior surface 14 of catheter tube 12.

Wall 366 of fitting 340, at the distal surface thereof contiguously receives a washer-shaped elastomeric wiping seal 400. Seal 400 comprises an outer annular edge 402 the diameter of which is substantially the same as the diameter of outside surface of wall 380. Washer 400 defines a central aperture 404 through which the catheter tube 12 passes. Aperture 404 has a diameter slightly less than the diameter of the exterior surface 14 of the catheter tube 12 so that a compression-fit relationship is created between the washer 400 and the exterior surface 14 of the catheter tube 12. This tight fit prevents flow of gas across surface 404 between the patient's airway and the interior of the flattened sheath 26. Washer 400 wipes any debris carried at the exterior surface 14 of the catheter tube 12 when and as the catheter tube is withdrawn from the respiratory system of the patient.

The seal/wiper 400 is held in the position illustrated in FIG. 9 between the proximal surface of wall 382 and the distal surface of the wall 366.

Formed as one piece with wall 382 is a distally-directed extension 386 comprising an annular wall the interior diameter of which is substantially larger than the diameter of the catheter tube 12 at surface 14. Thus, wall portion 386 creates a wash chamber 388. Wash chamber 388 is interrupted by a wash side port 390. Wash port 390 is aligned with the hollow interior 392 of a radially-directed wash tube 394. Irrigation solution may be introduced through the hollow interior 392 and the port 390 into the chamber 388, where the same is co-mingled or mixed with secretions and other debris, following which the mixture is removed through the hollow 16 of the catheter tube 12 when the distal tip 24 is disposed in the chamber 388 and a suction control valve is actuated so that vacuum pressure is delivered through the hollow interior 16 of the catheter tube 12 to the chamber 388. In normal use, an irrigation supply device can be connected to the radially-directed tube 394 to assist in the delivery of irrigation solution, under the control of a health care provider, to chamber 388. The length of the sheath 26 is selected so that withdrawal of the catheter tube 12 is limited such that distal tip 24 cannot be displaced to a location proximal of aperture 384.

Annular wall 386 merges with rounded tip wall 396. Wall 396 assists in centering the male member 342 for insertion into a manifold, adapter, fitting, or connector disposed at an exposed end of an indwelling tracheal tube, where the wall 386 may be glued, bonded, welded or the like in the assembled position. Tip wall 396 defines a circular aperture 398, the diameter of which is slightly greater than the diameter of catheter tube 12 at surface 14. Aperture 398 serves as a guide for the insertion of the catheter tube 12 into the respiratory tract of the patient.

The invention may be embodied in other specific forms without departing from the spirit of essential characteristics thereof. The present embodiments therefore to be considered in all respects as illustrative and are not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A catheter assembly for delivery respiratory therapy by way of aspiration of or delivery of fluids to a respiratory tract of an intubated patient, said catheter assembly comprising:

catheter means adapted for insertion into a respiratory tract of an intubated patient so as to be able to either aspirate the respiratory tract or deliver fluids to the respiratory tract;

a distal fitting slidably joined to said catheter means at one end thereof;

a proximal fitting non-slidably joined to said catheter means at an end opposite to said one end;

sheath means, having a distal end joined in a fluid tight fit to the distal fitting, and a proximal end joined in a fluid tight fit to the proximal fitting, for forming a single enclosed area that concentrically surrounds the catheter means between the distal and proximal fittings, said sheath means being collapsible in an accordion-like fashion when said catheter means is advanced through the distal fitting as the proximal and distal fittings slide toward one another;

means for forming a slidable seal around said catheter means at the distal fitting so as to prevent substantially any fluid from entering or exiting through said means from the enclosed area formed by said sheath means; and filter means for forming a gas permeable filter at said proximal fitting so as to prevent contaminants from entering or exiting the enclosed area through said filter means, said filter means accommodating the exit of gaseous fluids from the enclosed area as said sheath means collapses by moving the proximal end of the sheath means toward the distal end of the sheath means, and the reentry of gaseous fluids when gas is drawn into the enclosed area as said sheath means unfolds by moving the proximal end of the sheath means away from the distal end of the sheath means, said enclosed area being thereby protected from the passage of contaminating fluids into or out of the enclosed area by the combination of said slidable seal means and said filter means.

2. A catheter assembly for delivering respiratory therapy by way of aspiration of or delivery of fluids to a respiratory tract of an intubated patient, said catheter assembly comprising:

catheter means adapted for insertion into a respiratory tract of an intubated patient so as to be able to either aspirate the respiratory tract or deliver fluids to the respiratory tract;

sheath means for forming a single enclosed area that concentrically surrounds the catheter means along its length, said sheath means having distal and proximal ends and being collapsible in an accordion-like fashion when said catheter means is advanced into the respiratory tract, said single enclosed area being partially evacuated and sealed from the atmosphere so that said sheath means can be substantially fully collapsible without exhausting gas from said enclosed area as said catheter is advanced;

a distal fitting slidably joined to said catheter means at one end thereof, said distal fitting comprising distal collar means that compressively joins said distal end of the sheath means along a substantial length thereof in a substantially flat manner so as to thereby form a hermetic seal which prevents gaseous entry into or exit from said enclosed area at said distal fitting;

a proximal fitting non-slidably joined to said catheter means at an end opposite to said one end, said proximal fitting comprising proximal collar means that compressively joins said proximal end of the sheath means along a substantial length thereof in a substantially flat manner so as to thereby form a hermetic seal which prevents gaseous entry into or exit from said enclosed area at said proximal fitting; and sealing means for forming a slidable seal around said catheter means at the distal fitting so as to prevent substantially any fluid from entering or exiting through said sealing means from the enclosed area formed by said sheath means, said enclosed area being sealed and protected from passage of contaminating fluids into or out of the enclosed area by the combination of said slidable seal means, said proximal sleeve means and said distal sleeve means.

3. A method of manufacturing a catheter assembly for delivering respiratory therapy by way of aspiration of or delivery of fluids to a respiratory tract of an intubated patient, said method comprising the steps of:

obtaining catheter means adapted for insertion into a respiratory tract of an intubated patient so as to be able to either aspirate the respiratory tract or deliver fluids to the respiratory tract;

slidably joining a distal fitting to said catheter means at one end thereof;

non-slidably joining a proximal fitting to said catheter means at an end opposite to said one end;

providing flexible sheath means having a distal end and a proximal end;

surrounding said catheter means with said sheath means so as to form a single enclosed area that concentrically surrounds the catheter means between the distal and proximal fittings so that said sheath means is collapsible in an accordion-like fashion when said catheter means is advanced through the distal fitting as the proximal and distal fittings are moved toward one another;

partially evacuating said single enclosed area so that said sheath means can be substantially fully collapsed without the need to exhaust gas from said enclosed area as said proximal and distal fittings are moved toward one another;

sealing said sheath means along a substantial length of said proximal end and said distal end so as to thereby form a hermetic seal at each of said proximal and distal ends of said sheath means in order to prevent gaseous entry into or exit from said enclosed area so that said enclosed area is hermetically sealed from the atmosphere so as to prevent contaminants from entering said enclosed area as said proximal and distal fittings are moved toward one another; and forming a fluid tight fit between the distal end of the sheath means and the distal fitting and between the proximal end of the sheath means and the proximal fitting.

* * * * *